US008608925B2

United States Patent
King et al.

(10) Patent No.: US 8,608,925 B2
(45) Date of Patent: Dec. 17, 2013

(54) MULTIPLE-ELECTRODE IONIC PROBE

(75) Inventors: Karl King, Windsor, CO (US); John Robert Woodward, Windsor, CO (US); Russell Martin Young, Fort Collins, CO (US)

(73) Assignee: Hach Company, Loveland, CO (US)

( * ) Notice: Subject to any disclaimer, the term of this patent is extended or adjusted under 35 U.S.C. 154(b) by 177 days.

(21) Appl. No.: 12/682,913

(22) PCT Filed: Oct. 10, 2008

(86) PCT No.: PCT/US2008/079467
§ 371 (c)(1),
(2), (4) Date: Apr. 14, 2010

(87) PCT Pub. No.: WO2009/052022
PCT Pub. Date: Apr. 23, 2009

(65) Prior Publication Data
US 2010/0224490 A1    Sep. 9, 2010

Related U.S. Application Data

(60) Provisional application No. 60/981,344, filed on Oct. 19, 2007.

(51) Int. Cl.
*G01N 27/36* (2006.01)
*G01N 27/333* (2006.01)

(52) U.S. Cl.
USPC ........... 204/412; 204/416; 204/433; 204/435; 205/787.5; 205/789

(58) Field of Classification Search
USPC ................ 204/412, 416, 433, 435; 205/787.5
See application file for complete search history.

(56) References Cited

U.S. PATENT DOCUMENTS

| 4,196,383 | A | | 4/1980 | Teass, Jr. |
| 4,440,619 | A | | 4/1984 | Daroczy et al. |
| 4,650,562 | A | * | 3/1987 | Harman et al. ............... 204/420 |
| 5,124,659 | A | * | 6/1992 | Frola et al. ..................... 324/438 |
| 5,158,083 | A | | 10/1992 | Sacristan et al. |
| 5,502,388 | A | * | 3/1996 | Melzer .......................... 324/438 |
| 6,126,801 | A | | 10/2000 | Sokalski et al. |
| 6,353,323 | B1 | * | 3/2002 | Fuggle .......................... 324/438 |
| 6,551,478 | B1 | | 4/2003 | Bielawski et al. |
| 7,182,847 | B1 | | 2/2007 | Millar et al. |

FOREIGN PATENT DOCUMENTS

CN            1182877          *   5/1998
(Continued)

OTHER PUBLICATIONS

Green JACS 1933 55 (6) pp. 2331-2336.*
"Electromichemical Methods" Bard and Faulkner Eds., 1980, John Wiley and Sons pp. 73-79.*

(Continued)

*Primary Examiner* — Luan Van
*Assistant Examiner* — Steven Rosenwald
(74) *Attorney, Agent, or Firm* — Ference & Associates LLC

(57) ABSTRACT

A multiple-electrode ion meter (100) is provided. The multiple-electrode ion meter (100) includes meter electronics (102) configured to receive a plurality of ionic concentration voltage measurements and generate an ionic concentration measurement from the plurality of ionic concentration voltage measurements and three or more individual electrode units (108) in communication with the meter electronics (102). The three or more electrode units (108) generate the plurality of ionic concentration voltage measurements to the meter electronics (102).

8 Claims, 13 Drawing Sheets

(56) References Cited

FOREIGN PATENT DOCUMENTS

| DE | 29508870 | U1 |   | 9/1995 |
|----|----------|-----|---|--------|
| DE | 102004015084 |   | * | 8/2005 |
| DE | 102004015084 | A1 | * | 8/2005 |
| EP | 0299778 | A2 |   | 1/1989 |
| EP | 1710567 | A1 |   | 11/2006 |
| JP | SHO-57-103044 | A1 |   | 6/1982 |
| JP | HEI-01-112149 | A1 |   | 4/1989 |
| JP | HEI-06-242072 | A1 |   | 9/1994 |
| JP | HEI-09-178701 | A1 |   | 7/1997 |
| WO | 2006106071 | A1 |   | 10/2006 |

OTHER PUBLICATIONS

"Electromichemical Methods" Bard and Faulkner Eds., 1980, John Wiley and Sons p. 72.*

J.C. Seiter, M.D. Degrandpre: "Redundant chemical sensors for calibration-impossible applications" TALANTA, vol. 54, 2001, pp. 99-106, XP002508864 pp. 99, 100.

State Intellectual Property Office, P.R. China, Office Action for Multiple-Electrode Ionic Probe, May 8, 2012 (19 pages).

Yuanbo, Fang, Introduction to Three-Electrode pH Measurement System, Analytical Instrument, vol. 1 (44-46), Dec. 31, 1982, (4 pages).

* cited by examiner

MULTIPLE-ELECTRODE IONIC PROBE

BACKGROUND OF THE INVENTION

1. Field of the Invention

The invention is related to the field of ionic probes.

2. Statement of the Problem

A measure of the ionic concentration of a fluid is desirable in many situations, including testing of fluids in manufacturing settings, for pharmaceutical production, food processing and/or food quality, water quality testing, etc. Measurement of an ionic concentration or activity can indicate completion of a reaction, indicate fractions of components, etc.

One measure can comprise a measure of a pH concentration, which comprises a measure of acidity of the fluid being tested. The pH measurement can indicate the acidic or basic condition or concentration of the fluid.

A pH measurement comprises a measurement of hydrogen ions in a solution, expressed as a logarithmic number between about zero and fourteen (sometimes extending into negative numbers for exceedingly acidic solutions). On the pH scale, a very acidic solution has a low pH value, such as zero or one, corresponding to a large concentration of hydrogen ions ($H^+$). In contrast, a very basic solution has a high pH value, corresponding to a very small number of hydrogen ions (or to a correspondingly large number of $OH^-$ ions). A neutral solution, such as substantially pure water, has a pH value of about seven.

FIG. 1 shows a portion of a prior art pH meter probe including an active electrode and a reference electrode. The active electrode consists of a glass tube with an ion sensitive glass bulb at one end. The tube contains an electrolyte and an electrode. The glass on the exterior of the ion sensitive bulb exchanges ions with the fluid to be tested. This produces a charge in a hydrated layer on the outside of the bulb. The internal electrolyte interacts with the ion sensitive glass and reflects the potential developed by the ions at the outside of the glass.

The reference electrode is often included in a separate chamber and solution, and is also in ionic communication with the fluid being tested. A voltage potential between the two electrodes is thereby formed, similar to a battery. The voltage potential that is developed between the electrodes is directly related to the ion concentration of the solution. The reference electrode provides a stable potential against which the measuring electrode can be compared. The voltage potential can be processed according to a table, formula, or other algorithm to arrive at an ionic concentration measurement, such as a pH value, for example.

An ionic circuit is formed between the active electrode and a ground electrode, creating a measurable voltage potential. The reference potential is a known, substantially constant amount against which the process voltage (i.e., a voltage measurement) can be compared and interpreted by the prior art pH meter. The voltage potential between the active electrode and the reference electrode can be processed to determine an ionic concentration in the external test fluid.

The accuracy of ionic and/or pH measurements can be affected by various factors, including temperature and/or contaminated electrolyte solutions, for example. A common source of inaccuracy can be an improper or inaccurate reference signal generated from a reference electrode. If the reference signal is inaccurate, the resulting pH or ion measurement will be affected. Consequently, it is of great importance that a proper and accurate reference value be obtained.

The reference electrode is contained within a tube or chamber that includes an ionic bridge, such as a salt bridge, that enables ionic communication between the reference electrode and the external test fluid. However, the ionic bridge may allow some fluid exchange, enabling contamination of the internal buffer solution and possible poisoning of the internal reference electrode, and enabling contamination of the fluid to be measured.

A major problem with pH probes is in the junction between the internal fill solution of the reference electrode assembly and the external test fluid. Clogging or failure of the junction usually leads to very slow or erroneous readings. The junction can also allow the contamination of the fill solution with the measurement medium. This can degrade the reference electrode which then renders the pH probe inaccurate and it usually has to be replaced. One prior art solution has been the employment of multiple junctions and chambers between the reference electrode and the exterior medium. Another prior art solution has used flowing junctions in which a continuous supply of fill solution is fed to the reference electrode compartment and exits via a small hole or conduit. This has the advantage of preventing the contamination of the fill solution and the reference electrode but has the disadvantage of cumbersome plumbing to the electrode and the necessity to send the measurement medium to waste as it is contaminated with fill solution.

A newer approach has been to enclose both the active electrode and the reference electrode within an impermeable chamber, such as a glass chamber, for example. This is shown in U.S. Pat. No. 4,650,562 to Harman. The reference electrode 12 in Harman interfaces with the external test fluid through a pH sensitive glass bulb, similar to the structure of the active electrode 11. The external test fluid therefore cannot mingle with and contaminate the internal fill solution of the reference electrode.

SUMMARY OF THE INVENTION

A multiple-electrode ionic meter is provided. The multiple-electrode ionic meter comprises meter electronics configured to receive a plurality of ionic concentration voltage measurements and generate an ionic concentration measurement from the plurality of ionic concentration voltage measurements and three or more individual electrode units in communication with the meter electronics. The three or more electrode units generate the plurality of ionic concentration voltage measurements to the meter electronics.

A multiple-electrode ionic probe is provided. The multiple-electrode ionic probe comprises at least four electrode chambers, with the at least four electrode chambers being substantially sealed, and at least four corresponding ion sensitive regions formed in the at least four electrode chambers. The at least four ion sensitive regions enable ion interaction between the at least four electrode chambers and an exterior of the multiple-electrode ionic probe. The multiple-electrode ionic probe further comprises at least four corresponding electrodes positioned in the four electrode chambers.

A multiple-electrode ionic probe is provided. The multiple-electrode ionic probe comprises at least four electrode chambers, with the at least four electrode chambers being substantially sealed. A first pair of electrode chambers includes a first electrolyte solution and a second pair of electrode chambers includes a second electrolyte solution that is different from the first electrolyte solution. The multiple-electrode ionic probe further comprises at least four corresponding ion sensitive regions formed in the at least four electrode chambers. The at least four ion sensitive regions enable ion interaction between the at least four electrode chambers and an exterior of the multiple-electrode ionic probe. The multiple-electrode ionic probe further comprises at least four corresponding electrodes positioned in the four electrode chambers.

A multiple-electrode ionic probe is provided. The multiple-electrode ionic probe comprises at least four electrode chambers, with the at least four electrode chambers being substantially sealed, and at least four corresponding ion sensitive regions formed in the at least four electrode chambers. The at least four ion sensitive regions enable ion interaction between the at least four electrode chambers and an exterior of the multiple-electrode ionic probe. A first pair of electrode chambers includes a first pair of ion sensitive regions and a second pair of electrode chambers includes a second pair of ion sensitive regions that are different from the first pair of ion sensitive regions. The multiple-electrode ionic probe further comprises at least four corresponding electrodes positioned in the four electrode chambers.

ASPECTS

One aspect of the invention includes, a multiple-electrode ion meter, comprising:

meter electronics configured to receive a plurality of ionic concentration voltage measurements and generate an ionic concentration measurement from the plurality of ionic concentration voltage measurements; and three or more individual electrode units in communication with the meter electronics, with the three or more electrode units generating the plurality of ionic concentration voltage measurements to the meter electronics.

Preferably, the multiple-electrode ion meter further comprises a ground electrode.

Preferably, the multiple-electrode ion meter further comprises a housing including the three or more individual electrode units.

Preferably, the multiple-electrode ion meter with the three or more individual electrode units comprising:

three or more electrode chambers, with the three or more electrode chambers being substantially sealed;

three or more corresponding ion sensitive regions formed in the three or more electrode chambers, with the three or more ion sensitive regions enabling ion interaction between the three or more electrode chambers and an exterior of the multiple-electrode ionic probe; and three or more corresponding electrodes positioned in the three or more electrode chambers, with the three or more electrodes generating the plurality of ionic concentration voltage measurements to the meter electronics.

Preferably, the multiple-electrode ion meter with the three or more individual electrode units comprising:

four electrode chambers, with the four electrode chambers being substantially sealed;

four corresponding ion sensitive regions formed in the four electrode chambers, with the four ion sensitive regions enabling ion interaction between the four electrode chambers and an exterior of the multiple-electrode ionic probe; and four corresponding electrodes positioned in the four electrode chambers, with the four electrodes generating the plurality of ionic concentration voltage measurements to the meter electronics.

Preferably, the multiple-electrode ion meter with a first pair of electrode chambers includes a first electrolyte solution and with a second pair of electrode chambers including a second electrolyte solution, wherein the second electrolyte solution is different from the first electrolyte solution.

Preferably, the multiple-electrode ion meter with a first pair of electrode chambers includes a first electrolyte solution and with a second pair of electrode chambers including a second electrolyte solution, wherein the second electrolyte solution possesses a different ionic type or concentration than the first electrolyte solution.

Preferably, the multiple-electrode ion meter with a first pair of electrode chambers includes a first electrolyte solution and with a second pair of electrode chambers including a second electrolyte solution, wherein the second electrolyte solution possesses a different pH level than the first electrolyte solution.

Preferably, the multiple-electrode ion meter with a first pair of electrode chambers includes a first pair of ion sensitive regions and with a second pair of electrode chambers including a second pair of ion sensitive regions that are different from the first pair of ion sensitive regions.

Preferably, the multiple-electrode ion meter with a first pair of electrode chambers includes a first pair of ion sensitive regions and with a second pair of electrode chambers including a second pair of ion sensitive regions that include a second ionic sensitivity characteristic that is different from a first ionic sensitivity characteristic of the first pair of ion sensitive regions.

Another aspect of the invention comprises a multiple-electrode ionic probe, comprising:

at least four electrode chambers, with the at least four electrode chambers being substantially sealed;

at least four corresponding ion sensitive regions formed in the at least four electrode chambers, with the at least four ion sensitive regions enabling ion interaction between the at least four electrode chambers and an exterior of the multiple-electrode ionic probe; and at least four corresponding electrodes positioned in the four electrode chambers.

Preferably, the multiple-electrode ionic probe further comprises a ground electrode.

Preferably, the multiple-electrode ionic probe further comprises a housing including the at least four electrode chambers.

Preferably, the multiple-electrode ionic probe with a first pair of electrode chambers including a first electrolyte solution and with a second pair of electrode chambers including a second electrolyte solution and wherein the second electrolyte solution is different from the first electrolyte solution.

Preferably, the multiple-electrode ionic probe with a first pair of electrode chambers including a first electrolyte solution and with a second pair of electrode chambers including a second electrolyte solution, wherein the second electrolyte solution possesses a different ionic type or concentration than the first electrolyte solution.

Preferably, the multiple-electrode ionic probe with a first pair of electrode chambers including a first electrolyte solution and with a second pair of electrode chambers including a second electrolyte solution, wherein the second electrolyte solution possesses a different pH level than the first electrolyte solution.

Preferably, the multiple-electrode ionic probe with a first pair of electrode chambers including a first pair of ion sensitive regions and with a second pair of electrode chambers includes a second pair of ion sensitive regions that are different from the first pair of ion sensitive regions.

Preferably, the multiple-electrode ionic probe with a first pair of electrode chambers including a first pair of ion sensitive regions and with a second pair of electrode chambers including a second pair of ion sensitive regions that include a second ionic sensitivity characteristic that is different from a first ionic sensitivity characteristic of the first pair of ion sensitive regions.

Another aspect of the invention comprises a multiple-electrode ionic probe, comprising:

at least four chambers, with the at least four chambers being substantially sealed, with a first pair of chambers including a first electrolyte solution and with a second pair of chambers including a second electrolyte solution that is different from the first electrolyte solution;

at least four corresponding ion sensitive regions formed in the at least four chambers, with the at least four ion sensitive regions enabling ion interaction between the at least four chambers and an exterior of the multiple-electrode ionic probe; and at least four corresponding electrodes positioned in the four chambers.

Preferably, the multiple-electrode ionic probe further comprising a ground electrode.

Preferably, the multiple-electrode ionic probe further comprises a housing including the at least four electrode chambers.

Preferably, the second electrolyte solution possesses a different ionic type or concentration than the first electrolyte solution.

Preferably, the second electrolyte solution possesses a different pH level than the first electrolyte solution.

Preferably, the multiple-electrode ionic probe with a first pair of chambers including a first pair of ion sensitive regions and with a second pair of chambers including a second pair of ion sensitive regions that are different from the first pair of ion sensitive regions.

Preferably, the multiple-electrode ionic probe with a first pair of chambers including a first pair of ion sensitive regions and with a second pair of chambers including a second pair of ion sensitive regions that include a second ionic sensitivity characteristic that is different from a first ionic sensitivity characteristic of the first pair of ion sensitive regions.

Another aspect of the invention comprises a multiple-electrode ionic probe, comprising:

at least four chambers, with the at least four chambers being substantially sealed;

at least four corresponding ion sensitive regions formed in the at least four chambers, with the at least four ion sensitive regions enabling ion interaction between the at least four chambers and an exterior of the multiple-electrode ionic probe, with a first pair of chambers including a first pair of ion sensitive regions and with a second pair of chambers including a second pair of ion sensitive regions that are different from the first pair of ion sensitive regions; and at least four corresponding electrodes positioned in the four chambers.

Preferably, the multiple-electrode ionic probe further comprises a ground electrode.

Preferably, the multiple-electrode ionic probe further comprises a housing including the at least four electrode chambers.

Preferably, the multiple-electrode ionic probe with a first pair of electrode chambers including a first electrolyte solution and with a second pair of chambers including a second electrolyte solution and wherein the second electrolyte solution is different from the first electrolyte solution.

Preferably, the multiple-electrode ionic probe with a first pair of chambers including a first electrolyte solution and with a second pair of chambers including a second electrolyte solution, wherein the second electrolyte solution possesses a different ionic concentration than the first electrolyte solution.

Preferably, the multiple-electrode ionic probe with a first pair of chambers including a first electrolyte solution and with a second pair of chambers including a second electrolyte solution, wherein the second electrolyte solution possesses a different pH level than the first electrolyte solution.

Preferably, the multiple-electrode ionic probe wherein the second pair of ion sensitive regions include a second ionic sensitivity characteristic that is different from a first ionic sensitivity characteristic of the first pair of ion sensitive regions.

DESCRIPTION OF THE DRAWINGS

The same reference number represents the same element on all drawings. It should be understood that the drawings are not necessarily to scale.

DETAILED DESCRIPTION OF THE INVENTION

FIGS. 1-13 and the following description depict specific examples to teach those skilled in the art how to make and use the best mode of the invention. For the purpose of teaching inventive principles, some conventional aspects have been simplified or omitted. Those skilled in the art will appreciate variations from these examples that fall within the scope of the invention. Those skilled in the art will appreciate that the features described below can be combined in various ways to form multiple variations of the invention. As a result, the invention is not limited to the specific examples described below, but only by the claims and their equivalents.

Figure 1:
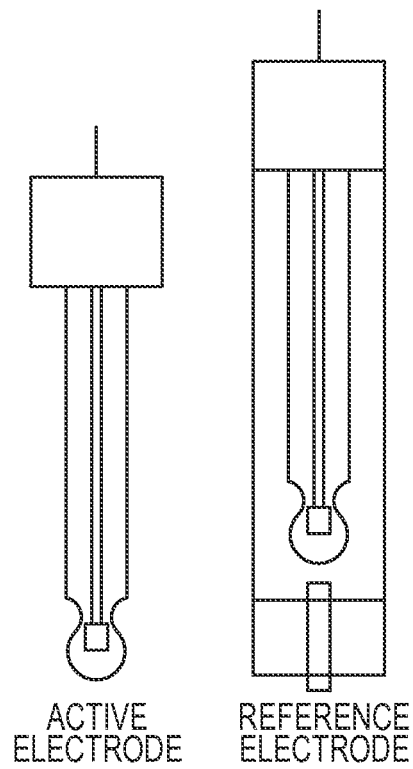
FIG. 1 shows a portion of a prior art pH meter probe including an active electrode and a reference electrode.
Figure 2:
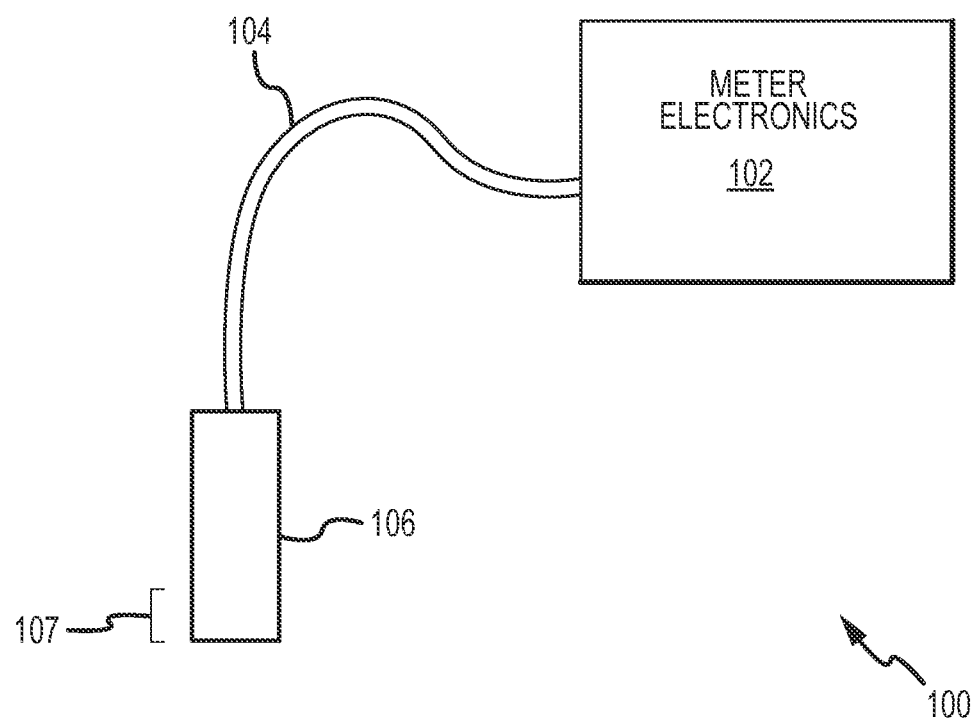
FIG. 2 shows an ion meter according to an embodiment of the invention.

FIG. 2 shows an ion meter 100 according to an embodiment of the invention. The ion meter 100 includes a multiple-electrode ionic probe 106, meter electronics 102, and a cable 104 connecting the multiple-electrode ionic probe 106 to the meter electronics 102. Alternatively, the ion meter 100 can be a wireless system and the multiple-electrode ionic probe 106 can communicate wirelessly with the meter electronics 102. The multiple-electrode ionic probe 106 can include a test end 107.

In use, the multiple-electrode ionic probe 106 is placed in an external test fluid. The test end 107 is contacted to or immersed in the external test fluid, although the entire multiple-electrode ionic probe 106 can be immersed. The external test fluid can comprise water, for example, although it should be understood that various other fluids can be tested. To that end, the multiple-electrode ionic probe 106 is immersed in and interacts with the sample fluid and generates a plurality of ionic voltage signals/measurements that are transferred to the meter electronics 102 by the cable 104. The plurality of ionic concentration voltage measurements generated by the multiple-electrode ionic probe 106 is related to an ion concentration within the external test fluid, such as a pH level, for example.

The meter electronics 102 receives the plurality of ionic concentration voltage measurements from the multiple-electrode ionic probe 106 and processes the signal in order to obtain an ionic concentration measurement, such as a pH value, for example. However, it should be understood that the ion meter 100 can detect and/or measure other ions and ion concentrations. The processing can include comparing the measurement voltage signal to a reference signal, wherein the ionic concentration measurement can be determined from a variation between a measurement voltage level of the active voltage signal and a voltage level of the reference signal from a reference electrode. Therefore, it is important that the reference signal be substantially steady at a given temperature in order to serve as a basis for all ionic concentration measurements. If the reference signal is not steady and constant, the resulting ionic concentration measurement will be inaccurate.

Figure 3:
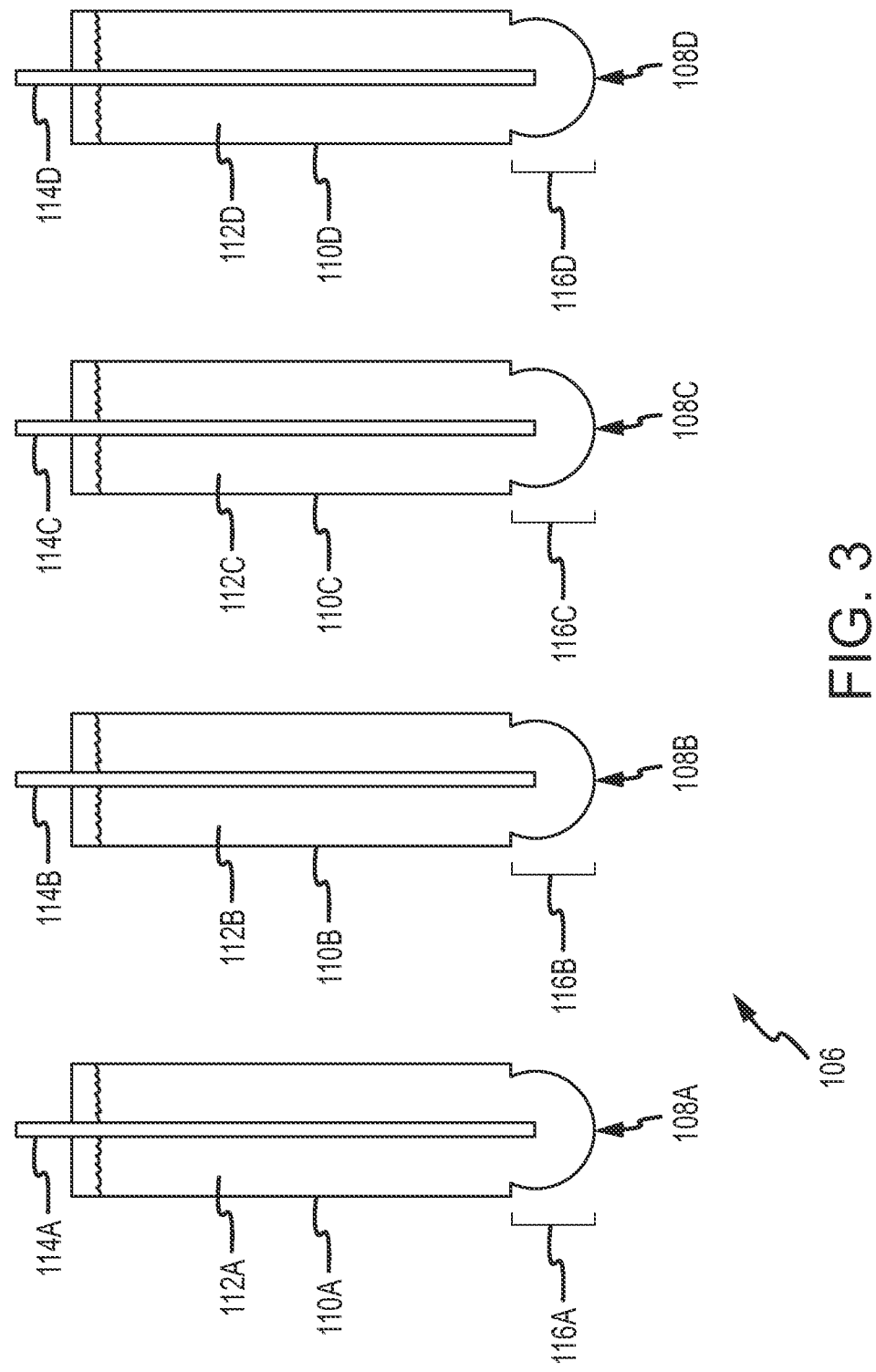
FIG. 3 shows a portion of the multiple-electrode ionic probe according to an embodiment of the invention.

According to the invention, the ionic probe 106 can include two or more active electrodes (see FIG. 3 and the accompanying discussion). In addition, the multiple-electrode ionic probe 106 can include two or more reference electrodes.

The ionic probe 106 can include additional components. For example, the ionic probe 106 can optionally include a preamp and/or other signal conditioning circuitry. The ionic probe 106 can include protective projections that extend from the test end 107, such as guard pins, bumps, ridges, etc. The ionic probe 106 can include a housing 120 (see FIG. 9) and any associated seals, potting material, desiccants, fillers, etc. The ionic probe 106 can include a ground electrode or element. The ionic probe 106 can include a temperature element. The ionic probe 106 can include mounting components or features. The ionic probe 106 can include electromagnetic interference shielding. Other components are contemplated for the ionic probe 106, and the above discussion is not an exhaustive listing.

FIG. 3 shows a portion of the multiple-electrode ionic probe 106 according to an embodiment of the invention. Components in common share reference numbers. The multiple-electrode ionic probe 106 in this embodiment includes at least four electrode units 108A-108D. The at least four electrode units 108A-108D can be used to generate ion concentration measurements, such as pH measurements, for example. Although the text focuses on four electrode units for the purpose of clarity, it should be understood that three or more electrode units can be employed.

Although only two electrode units and a ground are needed for obtaining an ionic concentration measurement, the at least four electrode units 108A-108D offer additional advantages. Multiple electrodes offer improved measurement accuracy through correlation of multiple measurement signals. Multiple electrodes offer improved measurement accuracy through the ability to compare measurement signals and reject outliers. Multiple electrodes offer the ability to detect problems in one or more of the electrode units. Multiple electrodes may be less sensitive to differences in temperature and other ambient characteristics.

The ionic voltage measurements generated by the three or more electrode units 108 can be processed in order to generate an ionic concentration measurement. The plurality of ionic concentration voltage measurements offer some redundancy and cross-correlation opportunities. The three or more electrode units 108 do not necessarily need to be labeled as being reference electrodes and active/measurement electrodes.

Each electrode unit 108 comprises an electrode chamber 110 including an ion sensitive region 116, an electrolyte solution 112 in the electrode chamber 110, and an electrode 114. The electrode chamber 110 can comprise any shape, including a substantially cylindrical shape, as shown. However, it should be understood that the electrode chambers 110 can comprise any desired shape, including oval, rectangular, or even irregular in cross-section, for example.

The electrode chambers 110 can be formed of any suitable material. The material must be substantially non-porous and must not permit fluid exchange between the interior and the exterior. In addition, the ion sensitive regions 116 must be able to be affixed to the material. In one embodiment, the electrode chambers 110 are formed of glass. However, other materials are contemplated and are within the scope of the description and claims. Advantageously, the electrodes 114 are sealed within the electrode chambers 110 and cannot be poisoned or affected by the external test fluid. Consequently, the electrode units 108 are substantially stable over time.

The ion sensitive regions 116 enable ion interaction by allowing ion exchange at the outer surface of the ion sensitive material, but do not permit a fluid exchange between the inside and the outside of the electrode chambers 110. There is a substantially constant charge on the inner surface of the ion sensitive material due to the fixed internal electrolyte solutions 112. The ion exchange in an outer hydrated layer of the ion sensitive material allows the development of a potential difference (i.e., a voltage potential) between an external test fluid and the internal electrolyte solution 112. The magnitude of this voltage potential is dependent on both the ionic value of the internal electrolyte solution and the ionic value of the external test fluid. For example, where the internal electrolyte solution has a pH value of seven and the external test fluid has a value of seven, the voltage potential will be substantially zero. Where the external test fluid has a pH value of four, a corresponding voltage potential will be developed at the electrode 114, typically about (−177) mV for a standard 59 mV/pH pH sensitive glass, for example.

The ion sensitive regions 116 comprise any manner of ion reactive material. For example, the ion sensitive regions 116 can be formed of an ion sensitive glass or pH sensitive glass. However, other ion sensitive materials are within the scope of the description and claims. The ion sensitive regions 116 can be chosen according to the external test fluid to be measured. The ion sensitive regions 116 in one embodiment comprise a specially formulated pH sensitive lithium ion-conductive glass consisting of the oxides of silica, lithium, calcium, and other elements. The structure of the pH glass allows lithium ion electrons to be exchanged by hydrogen ions in aqueous solutions, forming a hydrated layer on the outside surface of the ion sensitive regions 116. However, other materials are contemplated and are within the scope of the description and claims.

The ion sensitive regions 116 comprise portions of ion-sensitive material bonded into the respective electrode chambers 110. The ion sensitive regions 116 can be of any shape or size. The ion sensitive regions 116 can comprise projecting bulbs, as shown. Alternatively, the ion sensitive regions 116 can comprise substantially planar portions (see FIG. 9). It should be understood that other shapes and sizes are contemplated and are within the scope of the description and claims.

The ion sensitive regions 116 can be located at any position on the electrode chambers 110, such as at an end (shown). The ion sensitive regions 116 can be molded or bonded into apertures in the electrode chambers 110, for example. Alternatively, the ion sensitive regions 116 can be formed in the electrode chambers 110 during their formation, such as by glass blowing, for example.

The various ion sensitive regions 116 can be substantially similar, such as sharing common ionic interaction characteristics. One such ionic interaction characteristic comprises an ionic sensitivity characteristic. For example, a typical pH glass sensitivity in the prior art is about 59-60 millivolts per pH unit (mV/pH). Alternatively, the various ion sensitive regions 116 can be different, depending on the desired characteristics of the multiple-electrode ionic probe 106. The various ion sensitive regions 116 do not have to be of the same size, shape, thickness, composition, etc. For example, the ion sensitive region 116A can comprise an ion sensitive material possessing a lower ionic sensitivity than the ion sensitive region 116B.

The electrode chambers 110 are substantially filled with electrolyte solutions 112. An electrolyte solution 112 can comprise any solution that can communicate a voltage potential (on an ion sensitive region 116) to a corresponding electrode 114. An electrolyte solution 112 can comprise any desired ionic type or concentration. As discussed below, the ionic type or concentration of the electrolyte solution 112 can be selected in order to achieve the desired operation of the ion meter 100.

The electrodes 114 can be formed of any suitable material. In some embodiments, the electrodes 114 can be formed of silver/silver chloride, as is known in the art. However, other materials are contemplated and are within the scope of the description and claims.

In some embodiments, the electrodes 114 are located substantially on a central axis of the chambers 110, as shown. However, it should be understood that other arrangements are contemplated and are within the scope of the description and claims.

It should be understood that the multiple electrodes do not have to be identical. On the contrary, the electrode units 108 may differ in several ways. The electrode units 108 can include ion sensitive regions 116 possessing varying ionic response rates/ionic sensitivities. The electrode units 108 can be filled with electrolyte solutions 112 possessing differing properties, such as differing pH values, for example. This is discussed below in conjunction with FIG. 4.

Figure 4:
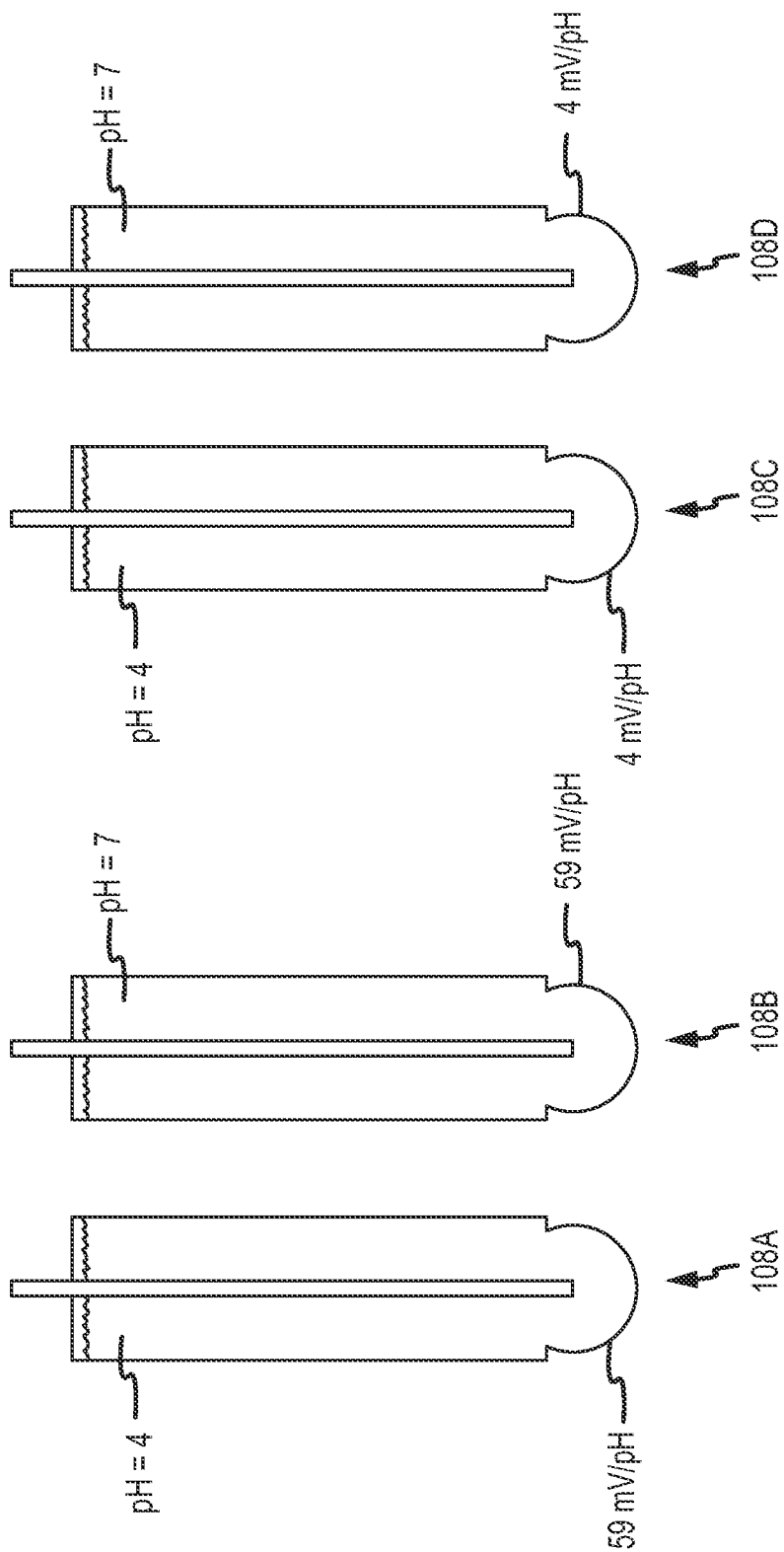
FIG. 4 shows the four electrode units according to an embodiment of the invention.

FIG. 4 shows the four electrode units 108A-108D according to an embodiment of the invention. In this embodiment, the four electrode units 108A-108D are organized into two pairs. In the first electrode pair, the electrode unit 108A has an ion sensitive region 116A of about 59 mV/pH ionic sensitivity and an electrolyte solution about 4 pH while the electrode unit 108B has an ion sensitive region 116B of about 59 mV/pH ionic sensitivity and an electrolyte solution of about 7 pH. The two electrolyte solutions of this pair can differ in ionic type and/or ionic concentration in order to be able to measure a pH of an external test fluid, for example. In the second electrode pair, the electrode unit 108C has an ion sensitive region 116C of about 4 mV/pH ionic sensitivity and an electrolyte solution of about 4 pH while the electrode unit 108D has an ion sensitive region 116D of about 4 mV/pH ionic sensitivity and an electrolyte solution of about 7 pH. The two electrolyte solutions of this pair can likewise differ in order to be able to separately measure a pH of the external test fluid.

The electrode units 108A and 108B therefore have similar ionic response characteristics and different electrolytes. Similarly, the electrode units 108C and 108D have similar ionic response characteristics and different electrolytes.

The electrode units 108A and 108B can be compared to each other in order to make a first ionic determination for an external test fluid and the electrode units 108C and 108D can be compared to each other in order to make a second, independent ionic determination.

The 59 mV/pH and 4 mV/pH values for the ion sensitive regions are merely illustrative and are not limiting. Any manner of ionic characteristics can be chosen for the ion sensitive regions. However, it is advantageous that the two pairs of electrode units have ionic characteristics that are distinct in order that comparisons can be made between the ionic voltage measurements. It should be understood that a significant response distance between the two pairs of electrode units will increase a signal-to-noise ratio and will improve the measuring capability of the ion meter 100.

Further, it is advantageous to provide a pair of electrode units with ionic responses as near to zero as possible. To that end, it has been found that heating a 59 mV/pH ion sensitive glass can reduce its ionic response down to as low as single digit ionic response values, such as the 4 mV/pH ionic glass shown in this embodiment. Other ionic response values are contemplated and are within the scope of the description and claims.

Figure 5:
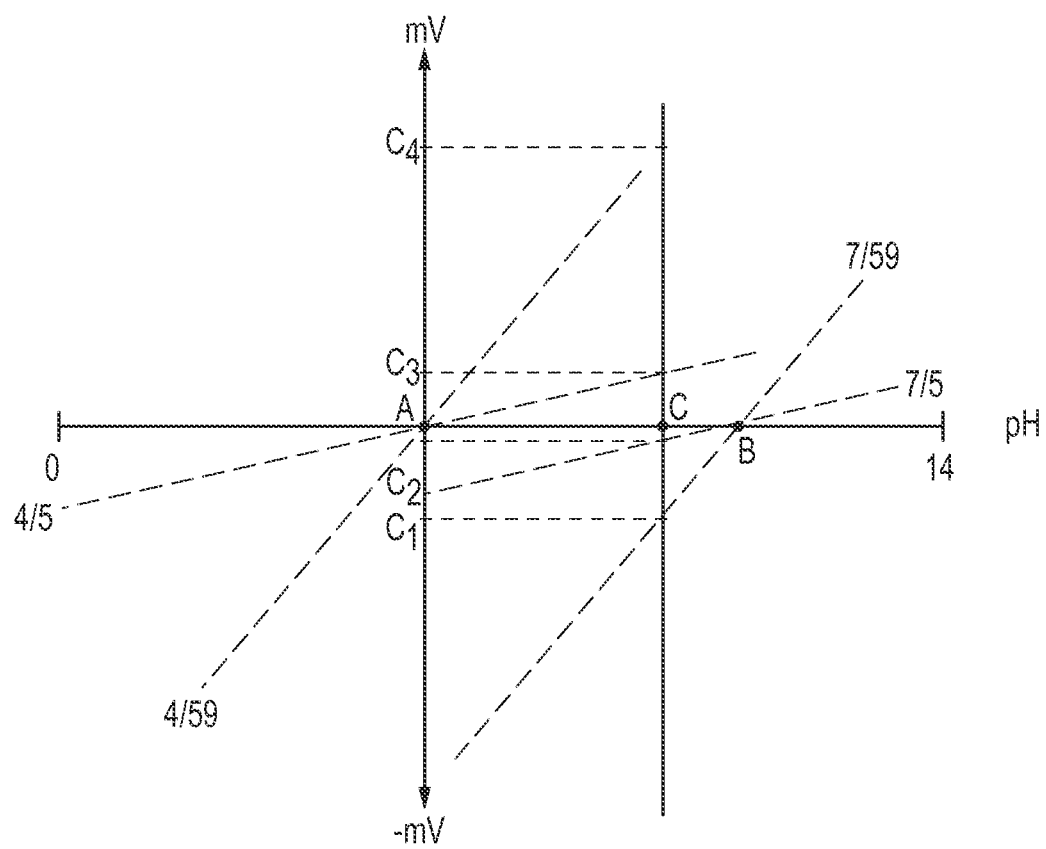
FIG. 5 is a graph of electrode unit characteristics according to an embodiment of the invention.

Reactions of these two electrode pairs in normal operation is shown and discussed in conjunction with FIG. 5. Reactions of these two electrode pairs in abnormal operation is shown and discussed in conjunction with FIGS. 6-8. It should be understood that the ion sensitive regions and electrolytes given in this example are merely for illustration and are not limiting in any manner.

While it may be possible to measure the pH of the external test fluid with less than four electrodes/values, the four electrode units provide cross-verification capabilities. For a single external test fluid, even an unknown ionic concentration fluid, the four voltage measurements should be in substantial agreement. A single outlier will be easily detected and can be appropriately handled.

The four electrode units 108A-108D further offer the ability to cross-check each other. Advantageously, the meter electronics 102 in some embodiments can automatically compensate for the slope of an ionic response (see FIG. 5). Further, the four electrode units 108A-108D can offer a lifetime calibration. If three of the four voltage measurements are in close agreement but one differs significantly, the ion meter 100 can determine that the differing measurement is not reliable and can choose to ignore any such measurements. Further, it is possible that if two of the measurements are significantly in error, the ion meter 100 can determine which two of the four can be not used for an ionic concentration measurement.

Alternatively, the electrode units 108A and 108D can be paired up for comparison, as can the electrode units 108B and 108C. Moreover, the two pairs (e.g., the pairs (108A-108B and 108C-108D) or (108A-108D and 108B-108C) can be compared in some embodiments.

It should be noted that the pair of electrode units 108A and 108B in this figure will not function for detecting an ionic concentration, as the ionic sensitivity is the same for both electrode units (i.e., 59 mV/pH versus 59 mV/pH). However, the pair of electrode units 108A and 108B can be used for diagnostic purposes.

FIG. 5 is a graph of electrode unit characteristics according to an embodiment of the invention. The horizontal axis represents pH values and the vertical axis represents a measured voltage in millivolts (mV). The four dashed lines of the graph represent the ionic response characteristics of four electrode units 108A-108D. At least one of the four electrode units 108A-108D is treated as a reference electrode unit. The reference electrode must have a different ionic sensitivity in order to be used as a reference voltage response (not required for a cross-checking operation). In this graph, two of the electrode units hold a first electrolyte solution, electrolyte A of about 4 pH, and the other two electrode units hold a second electrolyte solution of about 7 pH. The electrolyte A could have a pH level of four (point A on the graph) and electrolyte B could have a pH level of seven (point B). The two electrode units holding electrolyte A in this example have a pH sensitive glass of about 59 mV/pH and about 4 mV/pH. This is reflected in the slopes of the dashed lines for the two electrodes. The two electrode units holding electrolyte B likewise could include pH sensitive glass of about 59 mV/pH and about 4 mV/pH. As a result, for a specific external test fluid, each electrode will measure a different voltage potential. The four voltage potentials/voltage measurements can be used to determine an ionic concentration of the external test fluid.

The vertical line through point C is an example of one ionic concentration measurement. In this example, the external test fluid has a pH value of 6. Consequently, if the multiple-electrode ionic probe 106 is working properly, then it will generate voltage measurements of C1, C2, C3, and C4, as approximately shown. Due to the electrolyte B having a pH level of 7, the voltage measurements C1 and C2 will be negative voltage values (a pH of 6 being less than a pH of 7), while the C3 and C4 voltage measurements will be positive values (a pH of 6 being greater than a pH of 4).

The four voltage measurements can be cross-correlated to ensure that all four have expected values. For example, given C1-C3 in this example, it can be determined that the external test fluid has a pH level of 6. Consequently, the C4 value should be about 118 mV, given that the corresponding electrode unit has 59 mV/pH glass and an internal electrolyte of 4 pH, a difference of 2 pH (where 2 pH*59 mV/pH=118 mV). If the C4 measurement isn't about 118 mV, then the C4 measurement may be in error.

Figure 6:
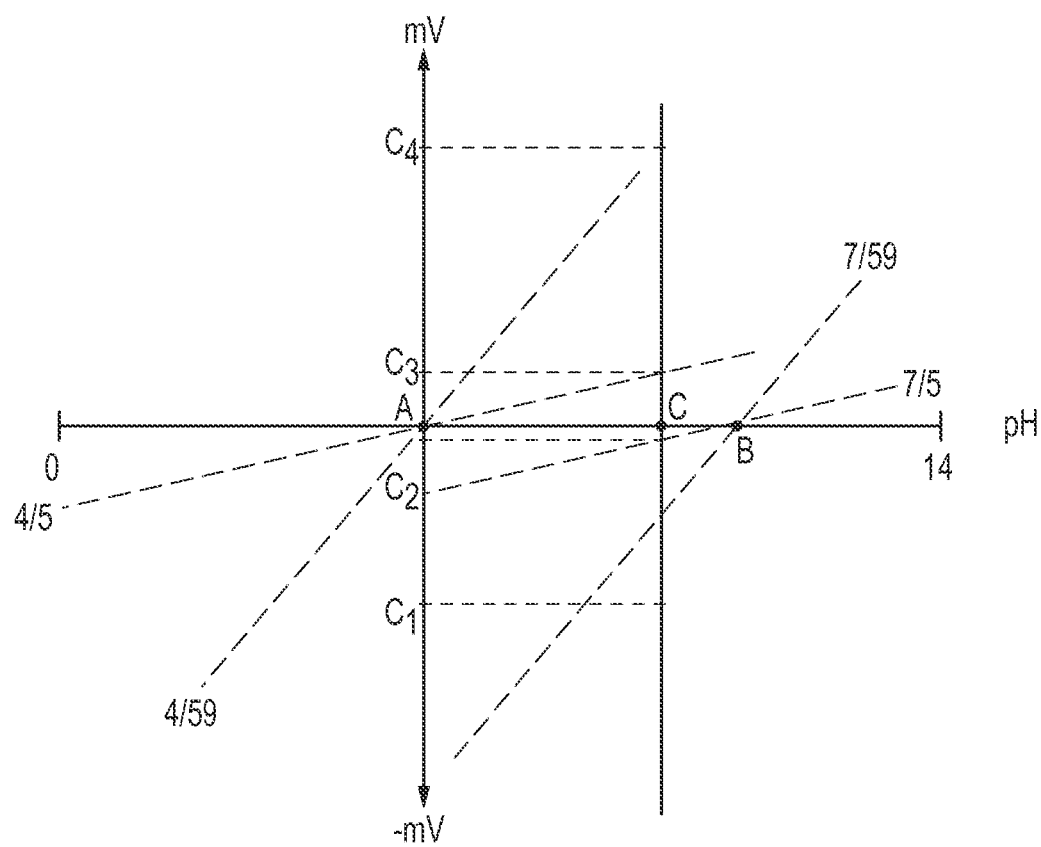
FIG. 6 shows a multiple-electrode ionic probe output example where a single voltage measurement is erroneous.

FIG. 6 shows a multiple-electrode ionic probe output example where a single voltage measurement is erroneous. The point C again reflects an external test fluid value of 6 pH. Here, the C1 measurement is a larger negative voltage than expected. As can be seen from the graph, the C1 voltage level should reflect an intersection of the 7/59 line and a value of 6 on the pH axis (i.e., the vertical line through point C). In this example, the C1 voltage measurement is significantly more negative than what it should be. Consequently, the C1 measurement can be logged, reported, and/or disregarded in subsequent ionic concentration measurements.

If a voltage measurement varies from an expected value by more than an error threshold or range, then the erroneous voltage measurement can be excluded from an ionic concentration measurement determination or can be compensated for or corrected in some manner. Here, the erroneous C1 voltage measurement can be left out of an ionic concentration measurement determination, if desired. Alternatively, the erroneous voltage measurement can be given a low weight or can be changed to place the measurement within an error threshold or range. Other compensations or corrections are contemplated and are within the scope of the description and claims.

Figure 7:
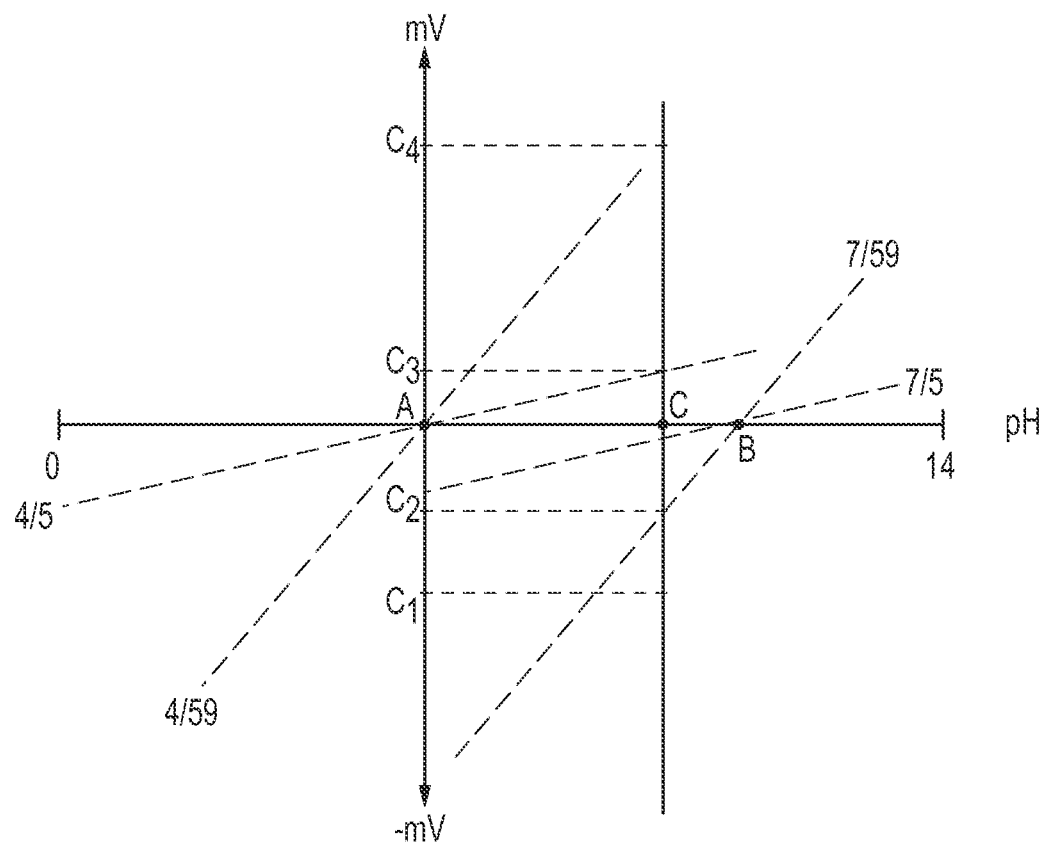
FIG. 7 shows a multiple-electrode ionic probe output example where two voltage measurements are erroneous.

FIG. 7 shows a multiple-electrode ionic probe output example where two voltage measurements are erroneous. The point C again reflects an external test fluid value of 6 pH. Here, the C1 and C2 measurements both appear to be inaccurate. The C1 voltage should correspond to an intersection of the 7/59 dashed line and the vertical line at C. The C2 voltage should correspond to an intersection of the 7/5 dashed line and the vertical line at C. Where the (C3, C4) pair indicates a pH of 6 for the external test fluid, but C1 and C2 don't uniformly disagree, it may be possible to determine that both C1 and C2 are generating erroneous readings. However, if the (C1, C2) electrode pair are in approximate agreement, it may not be possible to tell which of the electrodes are in error.

Figure 8:
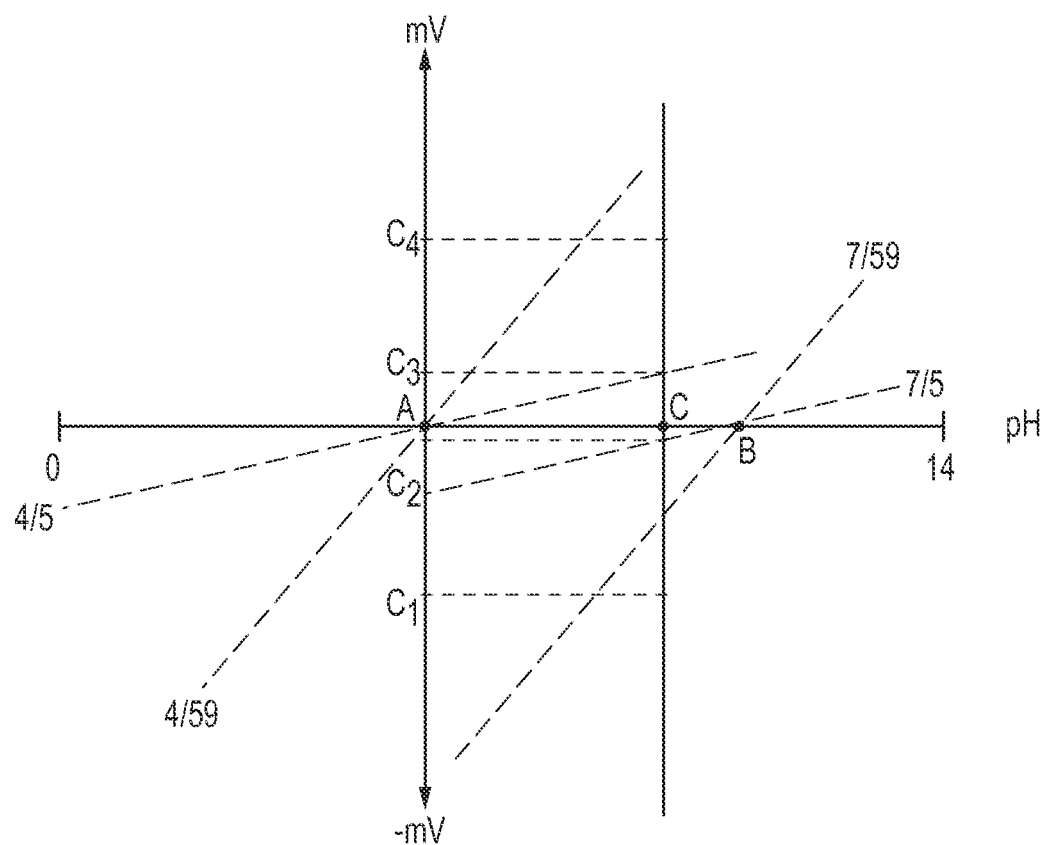
FIG. 8 shows another multiple-electrode ionic probe output example where two voltage measurements are erroneous.

FIG. 8 shows another multiple-electrode ionic probe output example where two voltage measurements are erroneous. The point C again reflects an external test fluid value of 6 pH. Here, the C1 and C4 measurements both appear to be inaccurate. In this scenario, the C2 and C3 measurements appear to be accurate. Again, if the C1 and C4 diverge from the C2 and C3 measurements, and differ from each other, it may be determined that the C1 and C4 measurements are problematic.

Figure 9:
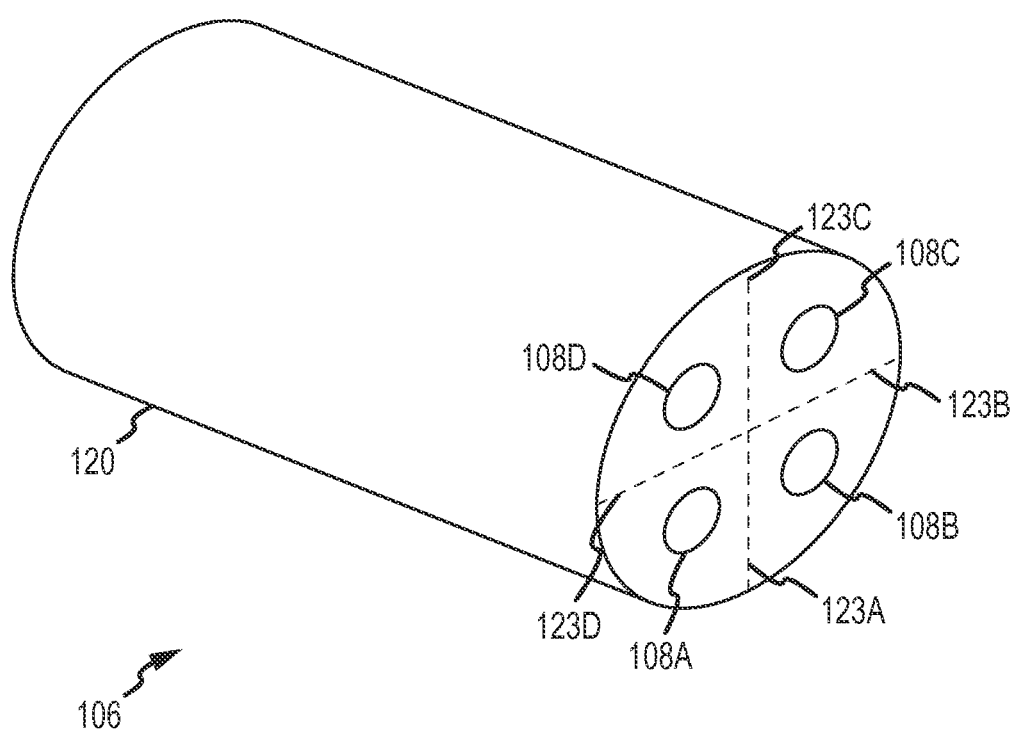
FIG. 9 shows an embodiment of the multiple-electrode ionic probe according to an embodiment of the invention.

FIG. 9 shows an embodiment of the multiple-electrode ionic probe 106 according to an embodiment of the invention. In this embodiment, the multiple-electrode ionic probe 106 includes the at least four electrode units 108A-108D (the ion sensitive regions 116A-116D are not labeled for the purpose of clarity). The cable 104 (see FIG. 2) can be connected to each of the electrodes 114/electrode units 108. The electrode units 108A-108D are positioned within a housing 120 so that at least a portion of the ion sensitive regions 116A-116D are exposed. The ion sensitive regions 116A-116D can comprise domed or projection portions of an ion sensitive material or can comprise a disc or plate of an ion sensitive material. The ion sensitive regions 116A-116D can be bonded to or otherwise affixed to the housing 120.

The ion sensitive regions 116A-116D can be formed as part of the electrode chambers 110A-110D. Alternatively, the housing 120 can include internal partitions 123A-123D that divide the housing 120 into chambers, wherein the ion sensitive regions 108A-108D can be affixed or formed into appropriate regions of the housing 120. Although four chambers and therefore four electrode units 108A-108D are shown, it should be understood that alternatively other numbers of electrode units 108 can be included in the multiple-electrode ionic probe 106.

Additional components can be included, such as one or more projections (not shown) that extend from the housing 120 and protect the electrode units 108. The multiple-electrode ionic probe 106 can further include features such as a ground electrode or ground region (not shown) and/or a shielding portion formed in the housing 120 or on an internal or external surface of the housing 120. For example, at least a portion of the housing 120 can comprise a metal shielding.

Figure 10:
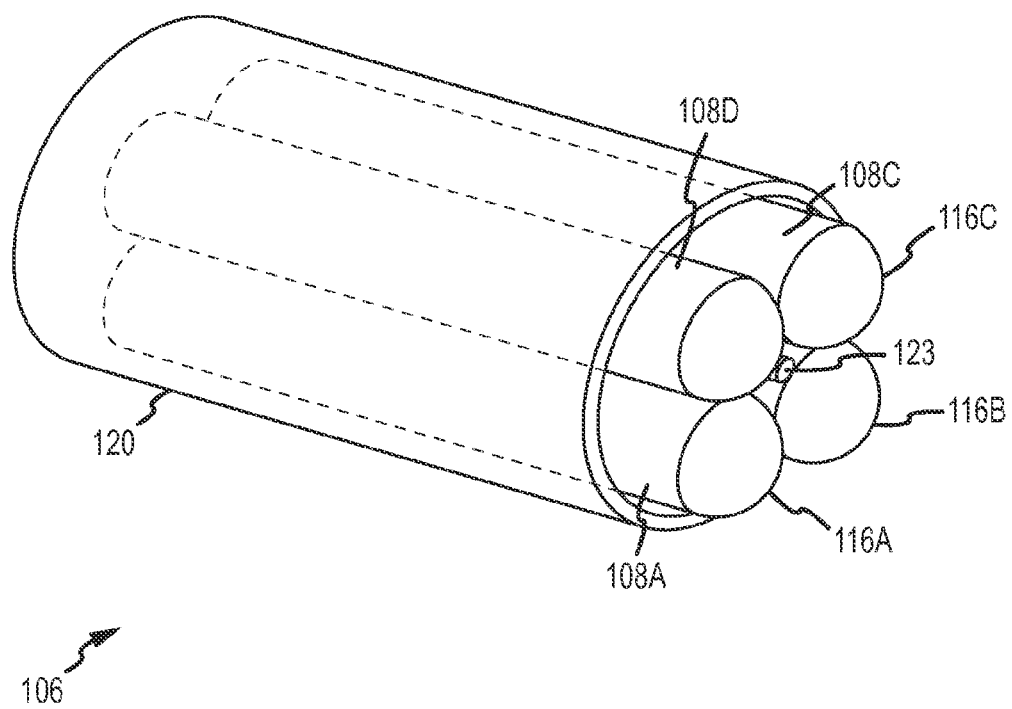
FIG. 10 shows an embodiment of the multiple-electrode ionic probe according to an embodiment of the invention.

FIG. 10 shows an embodiment of the multiple-electrode ionic probe 106 according to an embodiment of the invention. In this embodiment, the multiple-electrode ionic probe 106 comprises individual multiple electrode units 108 held within a housing 120. The cable 104 can be connected to each of the electrodes 114/electrode units 108. The multiple-electrode ionic probe 106 can further include a ground electrode 123. Each electrode unit 108 includes a corresponding ion sensitive region 116 and electrode 114 (not shown).

The housing 120 can comprise any manner of material and can be formed in any appropriate shape. In some embodiments, the multiple electrode units 108 are bonded or otherwise affixed in the housing 120. Alternatively, the multiple electrode units 108 can be held by a friction fit or can be trapped within the housing 120 in some manner.

Figure 11:
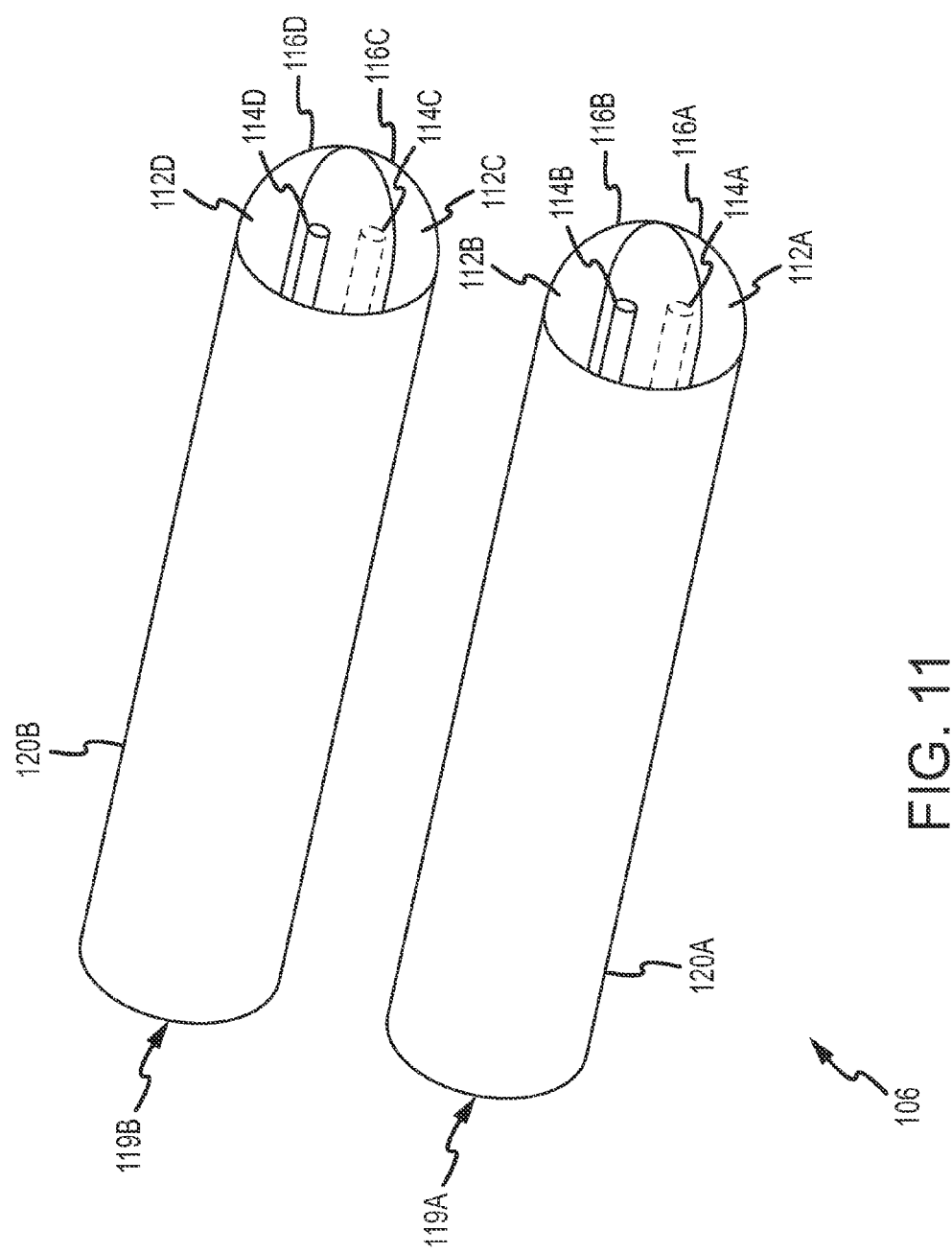
FIG. 11 shows an embodiment of the multiple-electrode ionic probe according to an embodiment of the invention.

FIG. 11 shows an embodiment of the multiple-electrode ionic probe 106 according to an embodiment of the invention.

In this embodiment, the multiple-electrode ionic probe 106 comprises two dual-electrode units 119A and 119B. Each dual-electrode unit 119 includes two electrolyte solutions (112A, 112B) or (112C, 112D), two ion sensitive regions (116A, 116B) or (116C, 116D), and two electrodes (114A, 114B) or (114C, 114D). Two of the dual-electrode units 119A and 119B therefore provide four of the electrode units 108A-108D, as previously discussed.

Figure 12:
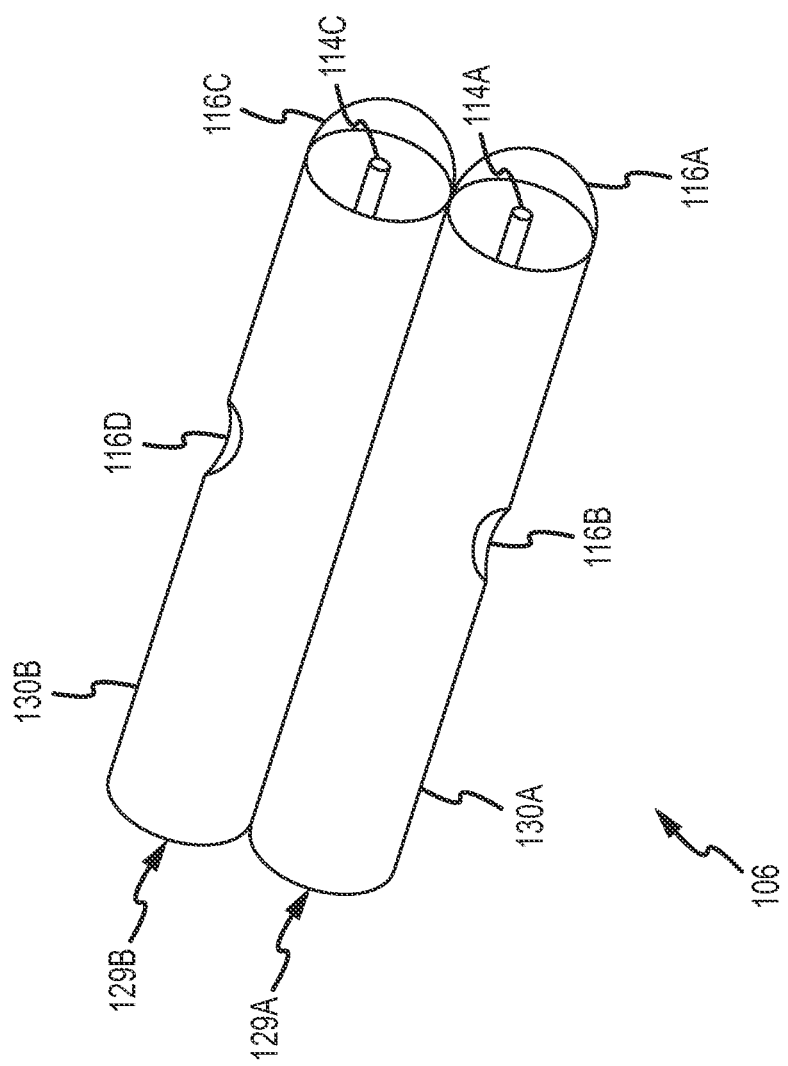
FIG. 12 shows an embodiment of the multiple-electrode ionic probe according to an embodiment of the invention.

FIG. 12 shows an embodiment of the multiple-electrode ionic probe 106 according to an embodiment of the invention. In this embodiment, the multiple-electrode ionic probe 106 comprises two dual-electrode units 129A and 129B. Each dual-electrode unit 129 includes housings 130A and 130B including two ion sensitive regions (116A, 116B) or (116C, 116D) and further includes active electrodes 114A and 114C and reference electrodes 114B and 114D (not shown, located inside the housings 130A or 130B adjacent to the ion sensitive regions 116B or 116D).

The two ion sensitive regions (116A, 116B) or (116C, 116D) can include a first ion sensitive region 116A or 116C on an end of a respective housing 130A or 130B and a second ion sensitive region 116B or 116D located on a side surface of the housing 130A or 130B. It can be seen from the figure that the ion sensitive regions are not restricted to ends of the respective electrode units 129A and 129B in this embodiment.

Figure 13A:
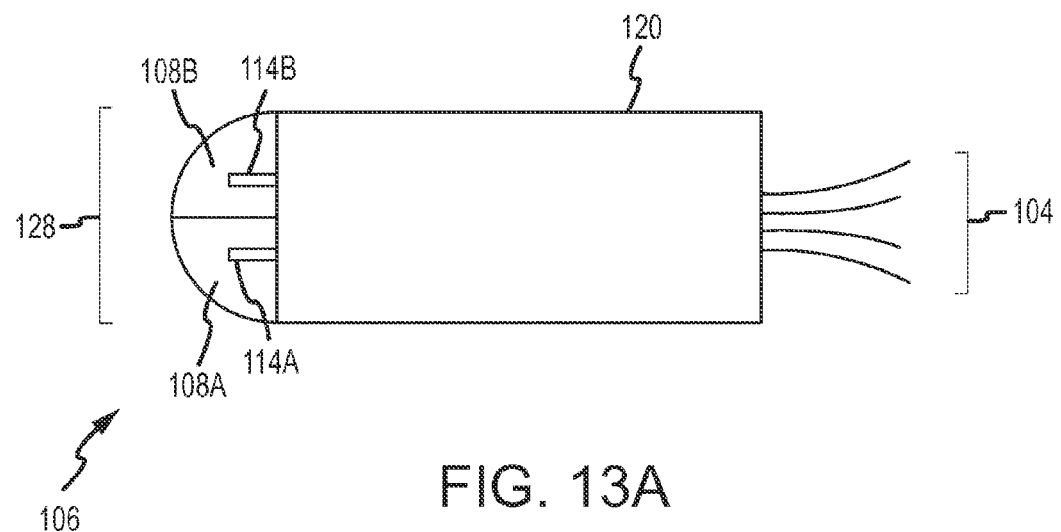
FIGS. 13A-13B show an embodiment of the multiple-electrode ionic probe according to an embodiment of the invention.
Figure 13B:
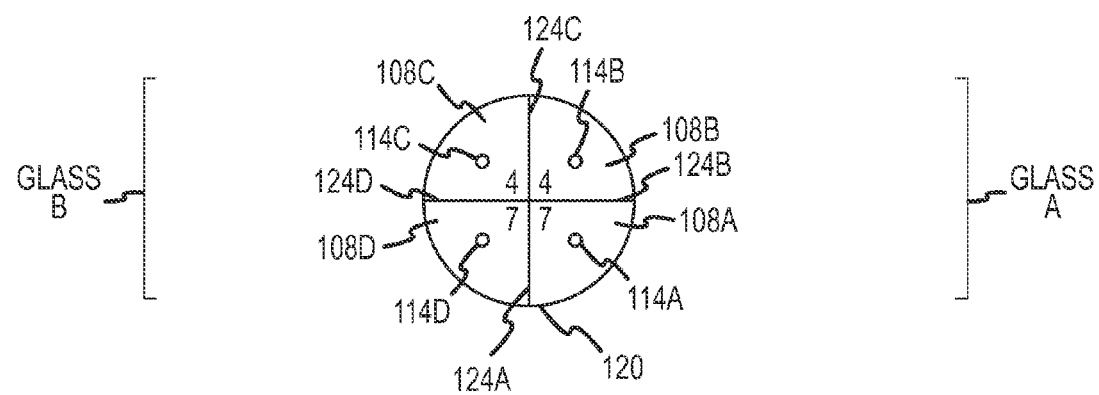

FIGS. 13A-13B show an embodiment of the multiple-electrode ionic probe 106 according to an embodiment of the invention. In this embodiment, the housing 120 includes partitions 124A-124D that divide the interior of the housing 120 into four chambers and therefore into the four electrode units 108A-108D. The ion sensitive regions 116A-116D (not labeled for purposes of clarity) can comprise domed or projection portions of an ion sensitive material, as previously discussed, and can form a bulb end 128. The inner partitions 124-127 can extend all of the way to the bulb end 128 and can be fused to the bulb end 128 so that four independent electrode chambers are formed within the housing 120. The cable 104 (see FIG. 2) can be connected to the electrodes 114A-114D within each of the electrode units 108.

In the embodiment shown, two of the electrode units comprise a solution of pH=4 and a glass type A and a glass type B, for example. The other two electrode units comprise a solution of pH=7 and a glass type A and a glass type B. It should be understood that the glass types can have different ionic sensitivities. Other ionic types and concentrations can be employed, and the above numbers are given merely for illustration.

We claim:

1. A multiple-electrode ionic probe, comprising:
    at least four chambers, with the at least four chambers being substantially sealed, with a first pair of chambers both including a first electrolyte solution and with a second pair of chambers both including a second electrolyte solution that is different from the first electrolyte solution;
    at least four corresponding ion sensitive regions formed in the at least four chambers, with the at least four ion sensitive regions enabling ion interaction between the at least four chambers and an exterior of the multiple-electrode ionic probe, with a first pair two of the chambers including an ion sensitive region having a first ionic sensitivity characteristic and with a second pair two of the chambers including an ion sensitive region having a second ionic sensitivity characteristic that differs from the first ionic sensitivity characteristic; and
    wherein both of a first chamber of the two chambers including an ion sensitive region having the first ionic sensitivity characteristic and a first chamber of the two chambers including an ion sensitive region having the second ionic sensitivity characteristic have the first electrolyte solution therein;
    wherein both of a second chamber of the two chambers including an ion sensitive region having the first ionic sensitivity characteristic and a second chamber of the two chambers including an ion sensitive region having the second ionic sensitivity characteristic have the second electrolyte solution therein; and
    at least four corresponding electrodes positioned in the at least four chambers;
    wherein the at least four chambers are measurement electrode chambers.

2. The multiple-electrode ionic probe of claim 1, further comprising a ground electrode.

3. The multiple-electrode ionic probe of claim 1, wherein the second electrolyte solution possesses a different ionic type or concentration than the first electrolyte solution or wherein the second electrolyte solution possesses a different pH level than the first electrolyte solution.

4. The multiple-electrode ionic probe of claim 1, wherein the at least four chambers provide potential differences that change with changing ion concentration of an exterior sample solution.

5. The multiple-electrode ionic probe of claim 1, wherein the at least four corresponding measurement electrodes each measure a different non-zero voltage potential for a given external sample solution.

6. The multiple-electrode ionic probe of claim 1, wherein the at least four chambers are formed of a substantially non-porous material.

7. The multiple-electrode ionic probe of claim 1, wherein the at least four corresponding ion-sensitive regions are formed of a substantially non-porous material.

8. The multiple-electrode ionic probe of claim 1, wherein the at least four corresponding ion-sensitive regions are formed of glass.

* * * * *